(12) United States Patent
Pind et al.

(10) Patent No.: US 8,889,395 B2
(45) Date of Patent: Nov. 18, 2014

(54) CRYSTAL METABOLITE RECOVERY

(75) Inventors: Peter Frode Pind, Herlev (DK); Simon Glanville, Kalundborg (DK); Sune Jakobsen, Vaerloese (DK); Svend Kaasgaard, Skovlunde (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/638,653

(22) PCT Filed: Mar. 25, 2011

(86) PCT No.: PCT/EP2011/054622
§ 371 (c)(1),
(2), (4) Date: Oct. 1, 2012

(87) PCT Pub. No.: WO2011/120882
PCT Pub. Date: Oct. 6, 2011

(65) Prior Publication Data
US 2013/0017592 A1  Jan. 17, 2013

Related U.S. Application Data

(60) Provisional application No. 61/346,630, filed on May 20, 2010.

(30) Foreign Application Priority Data

Mar. 30, 2010 (EP) ..................................... 10158417

(51) Int. Cl.
C12N 9/56 (2006.01)
C07K 1/14 (2006.01)
C07K 1/30 (2006.01)

(52) U.S. Cl.
CPC .. *C07K 1/30* (2013.01); *C07K 1/306* (2013.01)
USPC .......................................... 435/222; 530/412

(58) Field of Classification Search
USPC .......................................... 435/222; 530/412
See application file for complete search history.

(56) References Cited

U.S. PATENT DOCUMENTS 4,011,972 A * 3/1977 Pederson et al. ................. 494/41
2003/0129707 A1   7/2003 Nielsen

FOREIGN PATENT DOCUMENTS

| WO | 91/04318 A1 | 4/1991 |
| WO | 02/42767 A2 | 5/2002 |
| WO | 03/050274 A2 | 6/2003 |
| WO | 2006/056484 A1 | 6/2006 |
| WO | 2006/138520 A2 | 12/2006 |
| WO | 2008/110498 A1 | 9/2008 |

* cited by examiner

*Primary Examiner* — Suzanne M Noakes
(74) *Attorney, Agent, or Firm* — Michael W. Krenicky

(57) ABSTRACT

A method for producing a crystalline and/or amorphous metabolite suspension from a cell fermentation broth in a continuous centrifuge process comprising (a) adding at a separate inlet to the centrifuge the fermentation broth comprising the cells and the metabolite of interest, wherein the metabolite is partly or wholly on crystalline and/or amorphous form; (b) adding at another inlet to the centrifuge an aqueous liquid comprising a salt and/or a carbohydrate having a higher density than the cells and a lower density than the metabolite of interest in its precipitated form; (c) removing the cells at a separate outlet to the centrifuge; and (d) removing the suspension comprising the crystalline and/or amorphous metabolite of interest at another outlet to the centrifuge.

12 Claims, 1 Drawing Sheet

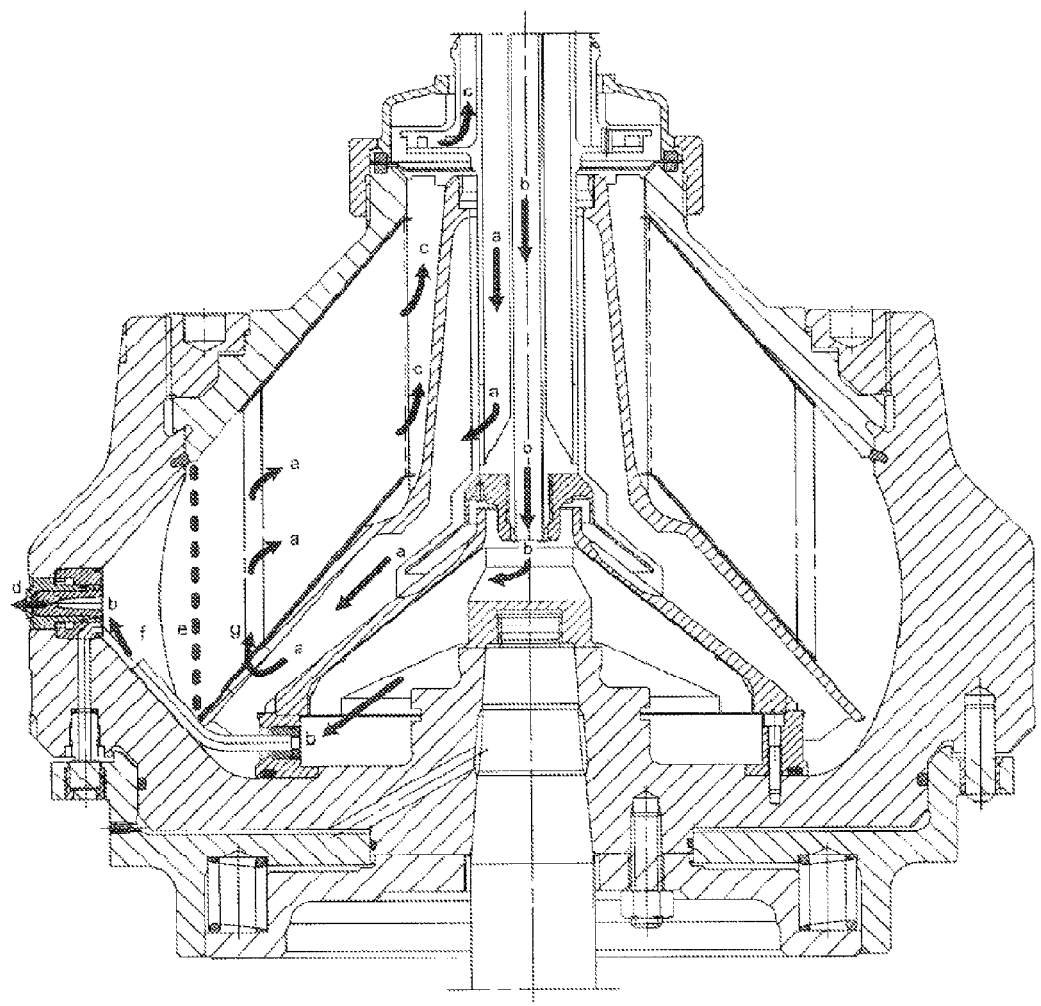

US 8,889,395 B2

CRYSTAL METABOLITE RECOVERY

CROSS-REFERENCE TO RELATED APPLICATIONS

This application is a 35 U.S.C. 371 national application of PCT/EP2011/054622 filed Mar. 25, 2011, which claims priority or the benefit under 35 U.S.C. 119 of European application no. 10158417.5 filed Mar. 30, 2010 and U.S. provisional application No. 61/346,630 filed May 20, 2010, the contents of which are fully incorporated herein by reference.

TECHNICAL FIELD

The present invention relates to a very effective method for obtaining a crystalline and/or amorphous metabolite suspension from a fermentation broth in a continuous centrifuge process.

BACKGROUND ART

The fermentation yield of industrial metabolites has increased dramatically over the last years. The yield of a metabolite such as a protease is now so high that more than 60% of the protease in the fermentation broth may be present as crystals and/or amorphous precipitate.

A number of methods have been applied for solving this problem of recovering the metabolite of interest in the most efficient way, see e.g., WO 2008/110498, wherein a method is disclosed comprising diluting the fermentation broth with water, adding a divalent salt, and adjusting the pH value of the fermentation broth to a pH value below pH 5.5.

The method disclosed in WO 2008/110498 demands a lot of water, so the purpose of this invention is to provide an efficient and less water demanding method to the above described problem.

SUMMARY OF THE INVENTION

It has surprisingly been found that a simple and effective method for producing a crystalline and/or amorphous metabolite suspension from a fermentation broth may be produced in a continuous centrifuge process comprising two inlets and two outlets. The method comprises:
(a) adding at a separate inlet to the centrifuge the fermentation broth comprising the cells and the metabolite of interest, wherein the metabolite is partly or wholly in crystalline and/or amorphous form;
(b) adding at another inlet to the centrifuge an aqueous liquid comprising a salt and/or a carbohydrate having a higher density than the cells and a lower density than the metabolite of interest in its precipitated form;
(c) removing the cells at a separate outlet to the centrifuge; and
(d) removing the suspension comprising the crystalline and/or amorphous metabolite of interest at another outlet to the centrifuge.

BRIEF DESCRIPTION OF DRAWINGS

FIG. 1 shows an Alfa Laval Separator Centrifuge model FEUX 510. The Centrifuge has been modified to a MBQX 510 model by installing 9 peripheral nozzles, and removing the UX-model paring tube holder.

DETAILED DISCLOSURE OF THE INVENTION

The present invention provides a simple and effective method for producing a crystalline and/or amorphous metabolite suspension from a fermentation broth.

The method of the invention may be applied to an untreated fermentation broth, i.e., to a fermentation broth taken directly from a fermentor with no dilution, no addition of any chemicals and no temperature adjustment. The method of the invention may also be applied to a fermentation broth that has first been subjected to, e.g., a pH adjustment and/or a temperature adjustment and/or a dilution.

Metabolites of Interest

The metabolite of interest according to the invention may be a commodity chemical such as citric acid or amino acids. The metabolite may also be a protein, e.g., a therapeutic protein such as insulin or an enzyme. The enzyme may be a hydrolase, a transferase, a lyase, an isomerase, an oxidoreductase, or a ligase.

In a preferred embodiment, the method is applied to proteases, lipases, amylases, cellulases, mannanases, and oxidoreductases.

Proteases

In a preferred embodiment the protease is a subtilisin or a metallo protease.

A subtilisin is a serine protease that uses a catalytic triad composed of Asp32, His64 and Ser221 (subtilisin BPN' numbering). It includes any enzyme belonging to the NC-IUBMB enzyme classification: EC 3.4.21.62.

A subtilisin may according to the peptidase classification be described as: clan SB, family S8, MEROPS ID: S08.001.

Subtilisins are described in, e.g., Barrett et al. 1998. Handbook of proteolytic enzymes. Academic press, p. 289-294.

There are no limitations on the origin of the protease of the invention and/or for the use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared as is generally known in the art, e.g., by site-directed mutagenesis, by PCR (using a PCR fragment containing the desired mutation as one of the primers in the PCR reactions), or by random mutagenesis. The preparation of consensus proteins is described in, e.g., EP 897985.

A preferred subtilisin is a subtilisin selected from the group consisting of subtilisin Carlsberg, subtilisin BPN', subtilisin 147, subtilisin 309, and subtilisin 1168.

Preferred commercially available proteases include NEUTRASE™, ALCALASE™, SAVINASE™, EVPERASE™, EVERLASE™, OVOZYME™, CORONASE™, POLARZYME™, and KANNASET™ (Novozymes NS); MAXATASE™, MAXACAL™, MAXAPEM™, PROPERASE™, PURAFECT™, PURAFECT OXP™, FN2™, FN3™, and FN4™ (Genencor International Inc.); and BLAP X™ (Henkel).

Amylases

Suitable amylases (alpha and/or beta) include those of bacterial origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Natalase™, Termamyl LC™, Termamyl SC™, Liquizyme-X™, BAN™, Stainzyme™, and Stainzyme Plus™, (Novozymes NS), Rapidase™, Purastar™, and Powerase™ (from Genencor International Inc.).

Cellulases

Suitable cellulases include those of bacterial or fungal origin. Chemically modified or protein engineered mutants are included (including substitutions, insertions, and/or deletions). Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Oxidoreductases

Oxidoreductases that may be treated according to the invention include peroxidases (EC 1.11.1.7), and oxidases such as laccases, and catalases (EC 1.11.1.6).

Cell fermentation broth

The fermentation broth according to the invention comprises the cells producing the metabolite of interest, and the metabolite of interest partly present as crystals and/or amorphous precipitate.

According to the present invention at least 40% of the metabolite of interest is present as crystals and/or amorphous precipitate; preferably at least 45% of the metabolite of interest is present as crystals and/or amorphous precipitate; preferably at least 50% of the metabolite of interest is present as crystals and/or amorphous precipitate; preferably at least 55% of the metabolite of interest is present as crystals and/or amorphous precipitate; preferably at least 60% of the metabolite of interest is present as crystals and/or amorphous precipitate; preferably at least 65% of the metabolite of interest is present as crystals and/or amorphous precipitate; preferably at least 70% of the metabolite of interest is present as crystals and/or amorphous precipitate; preferably at least 75% of the metabolite of interest is present as crystals and/or amorphous precipitate; preferably at least 80% of the metabolite of interest is present as crystals and/or amorphous precipitate; preferably at least 85% of the metabolite of interest is present as crystals and/or amorphous precipitate; preferably at least 90% of the metabolite of interest is present as crystals and/or amorphous precipitate; in particular at least 95% of the metabolite of interest is present as crystals and/or amorphous precipitate.

Any cell known in the art may be used. The cell may be a microorganism or a mammalian cell. The microorganism according to the invention may be a microorganism of any genus.

In a preferred embodiment, the metabolite of interest may be obtained from a bacterial or a fungal source.

For example, the metabolite of interest may be obtained from a gram positive bacterium such as a *Bacillus* strain, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis*; or a *Streptomyces* strain, e.g., *Streptomyces lividans* or *Streptomyces murinus*; or from a gram negative bacterium, e.g., *E. coli* or *Pseudomonas* sp. In a preferred embodiment the cell is a *Bacillus* cell.

The metabolite of interest may be obtained from a fungal source, e.g. from a yeast strain such as a *Candida, Kluyveromyces, Pichia, Saccharomyces, Schizosaccharomyces*, or *Yarrowia* strain, e.g., *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* strain.

The metabolite of interest may be obtained from a filamentous fungal strain such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* strain, in particular the polypeptide of interest may be obtained from an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenaturn, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* strain.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

For purposes of the present invention, the term "obtained from" as used herein in connection with a given source shall mean that the metabolite of interest is produced by the source or by a cell in which a gene from the source has been inserted.

The cells may be fermented by any method known in the art. The fermentation medium may be a complex medium comprising complex nitrogen and/or carbon sources, such as soybean meal, cotton seed meal, corn steep liquor, yeast extract, casein hydrolysate, molasses, and the like. The fermentation medium may be a chemically defined media, e.g. as defined in WO 98/37179.

The fermentation may be performed as a fed-batch, a repeated fed-batch or a continuous fermentation process.

In a preferred embodiment the cells of the invention are single cells. Some fungi may be produced in a yeast-like form. The fungi cells may also be fragmented and/or disrupted as described in WO 2005/042758.

Adjustment of pH

The pH of the fermentation broth may be adjusted before the continuous centrifuge process to an optimum pH wherein the metabolite is most stable and/or has the lowest solubility.

A way of finding this optimum is to run a trial, typically starting at pH 11, then perform the test at pH 10, then perform the test at pH 9, then at pH 8, then at pH 7, and so on down to pH 3, and then, if the optimum, e.g., is between pH 4 and pH 5, then do a trial within this range whereby the optimum pH is found; the optimum will normally be in the range between pH 4 and pH 11.

For adjustment of pH virtually any acid or base can be used. The acid may be inorganic or organic. Some examples are hydrochloric acid, sulphuric acid, sulphurous acid, nitrous acid, phosphoric acid, acetic acid, citric acid, and formic acid. Preferred acids are phosphoric acid, formic acid, citric acid, and acetic acid. Preferred bases are sodium hydroxide, potassium hydroxide, calcium hydroxide, and ammonium hydroxide, in particular sodium hydroxide.

Adjustment of temperature

The temperature of the fermentation broth may be adjusted before the continuous centrifuge process in order to find the optimum wherein the metabolite is most stable and/or has the lowest solubility.

A way of finding this optimum is to run a trial, typically starting at 5° C., then perform the test at 10° C., then at 20° C., then at 30° C., then at 40° C., then at 50° C., then at 60° C., and then at 70° C.; and then, if it is found, e.g., that the optimum is between 30° C. and 40° C., then do a trial within this range whereby the optimum temperature is found.

Separation equipment

According to the invention an example of appropriate separation equipment is a continuous centrifuge process, e.g., a two-phase centrifuge, especially a continuous sludge discharging centrifuge. The centrifuge may be bought from, e.g., Alfa Laval or Westfalia Separators.

The present invention comprises a method with the following steps:
(a) adding at a separate inlet to the centrifuge the fermentation broth comprising the cells and the metabolite of interest, wherein the metabolite is partly or wholly in crystalline and/or amorphous form;
(b) adding at another inlet to the centrifuge an aqueous liquid comprising a salt and/or a carbohydrate having a higher density than the cells and a lower density than the metabolite of interest;
(c) removing the cells at a separate outlet to the centrifuge; and
(d) removing the suspension comprising the crystalline and/or amorphous metabolite of interest at another outlet to the centrifuge.

In particular the present invention comprises a method with the following steps:
(a) adding at a separate inlet to the centrifuge the fermentation broth comprising the cells and the metabolite of interest, wherein the metabolite is partly or wholly in crystalline and/or amorphous form;
(b) adding at another inlet to the centrifuge an aqueous liquid comprising a salt and/or a carbohydrate having a higher density than the cells and a lower density than the metabolite of interest in its precipitated form;
(c) removing the cells at a separate outlet to the centrifuge; and
(d) removing the suspension comprising the crystalline and/or amorphous metabolite of interest at another outlet to the centrifuge.

FIG. 1 shows a preferred embodiment using an Alfa Laval Separator Centrifuge model FEUX 510. The Centrifuge has been modified to a MBQX 510 model by installing 9 peripheral nozzles, removing the UX-model paring tube holder, and using the concentrate outlet pipes as the heavier liquid inlet pipes.

In a preferred embodiment the interface (e) (see FIG. 1) between the fermentation broth liquid and the aqueous heavier liquid is formed between the internal inlet radius point (f) of the aqueous heavier liquid and the inlet radius (g) of the fermentation broth liquid.

In the preferred embodiment the centrifuge is equipped with a disc stack where the main feed is added to peripheral slots in the discs. Thus ensuring that interface (e) is not entering the disc stack where a smaller interface area can reduce capacity. For the illustrated centrifuge in FIG. 1, this has been accomplished by replacing the standard disc stack with rising channels internally in the discs with a smaller diameter disc with slots instead.

In a preferred embodiment the suspension comprising the crystalline and/or amorphous metabolite of interest is concentrated a factor 1.1-20 compared to the cell fermentation broth; preferably the crystalline and/or amorphous metabolite of interest is concentrated a factor 1.2-20 compared to the cell fermentation broth; preferably the crystalline and/or amorphous metabolite of interest is concentrated a factor 1.3-20 compared to the cell fermentation broth; preferably the crystalline and/or amorphous metabolite of interest is concentrated a factor 1.4-20 compared to the cell fermentation broth; preferably the crystalline and/or amorphous metabolite of interest is concentrated a factor 1.5-20 compared to the cell fermentation broth; preferably the crystalline and/or amorphous metabolite of interest is concentrated a factor 1.6-20 compared to the cell fermentation broth; preferably the crystalline and/or amorphous metabolite of interest is concentrated a factor 1.7-20 compared to the cell fermentation broth; preferably the crystalline and/or amorphous metabolite of interest is concentrated a factor 1.8-20 compared to the cell fermentation broth; preferably the crystalline and/or amorphous metabolite of interest is concentrated a factor 1.9-20 compared to the cell fermentation broth; preferably the crystalline and/or amorphous metabolite of interest is concentrated a factor 2-20 compared to the cell fermentation broth; in particular the crystalline and/or amorphous metabolite of interest is concentrated a factor 2-10 compared to the cell fermentation broth.

In a preferred embodiment the outlet from the centrifuge comprising the crystalline and/or amorphous metabolite of interest is re-circulated to the liquid inlet (step (b)). The re-circulation may take place as many times as needed. A re-circulation of 2 or 3 times will normally be adequate.

The soluble part of the metabolite of interest may be recovered by conventional means after first isolating the fraction that is precipitated.

Salts

The aqueous liquid may comprise a salt. Preferred salts are: magnesium, sodium, potassium, ammonium or calcium salts of chloride, citrate, acetate, formiate or sulphate, e.g., $MgCl_2$, $CaCl_2$, $NaCl$, $KCl$, $NH_4Cl$, $MgSO_4$, $Na_2SO_4$, $K_2SO_4$, or $(NH_4)_2SO_4$.

Carbohydrates

The aqueous liquid may comprise a carbohydrate.

Any carbohydrate as defined in John F. Robyt: Essentials of Carbohydrate Chemistry, p. 2 (1998): "the modern definition of a carbohydrate is that it is a polyhydroxy aldehyde or ketone, or a compound that can be derived from them by any of several means including (1) reduction to give sugar alcohols, (2) oxidation to give sugar acids; (3) substitution of one or more of the hydroxyl groups by various chemical groups, for example, hydrogen [H] may be substituted to give deoxysugars, and amino group [$NH_2$ or acetyl-NH] may be substituted to give amino sugars; (4) derivatization of the hydroxyl groups by various moieties, for example, phosphoric acid to give phosphor sugars, or sulphuric acid to give sulfo sugars, or reaction of the hydroxyl groups with alcohols to give saccharides, oligosaccharides, and polysaccharides."

The carbohydrates contemplated in this invention are having four or more carbon atoms; preferably from 4 to 12 carbon atoms; in particular from 4 to 6 carbon atoms.

According to the present invention a polyhydroxy aldehyde or a ketone is preferred.

In particular a mono-saccharide selected from the group consisting of glucose, fructose, mannose and galactose is preferred.

Of the substituted sugars, methyl glycosides, N-acetyl-glucosamine, N-acetyl-galactosamine and their de-acetylated forms are preferred.

In another preferred embodiment a di-saccharide selected from the group consisting of lactose, maltose, isomaltose, trehalose, maltulose, cellobiose, and sucrose is preferred.

Among the oligosaccharides, dextrins, limit dextrins, cyclodextrins, and amylopectins are preferred. The sugar acids may include both "uronic" and "onic" acids such as gluconic acid, glucuronic acid and galacturonic acid.

Polyols

Any polyol may be used. However, a polyol selected from the group derived from the carbohydrates having at least three carbon atoms are preferred. These have the general formula $C_nH_{2n+2}O_n$, wherein n is from 3 to 8 carbon atoms; in particular n is from 3 to 6 carbon atoms.

Polyols include but are not limited to sorbitol, mannitol, erythritol, ribitol, and xylitol.

In another preferred embodiment the polyol is glycerol or 1,3-propane diol or 1,2-propane diol (also often referred to as monopropylene glycol or MPG).

Derivatives

Derivatives that may be used according to the invention include methyl glycosides, glucoronic acids, amino sugars, or N-acetyl glucosamines.

The aqueous liquid having a higher density than the cells and a lower density than the metabolite of interest The aqueous liquid may comprise a salt; or a carbohydrate; or a polyol; or any combinations hereof such as a salt and a carbohydrate; or a salt and a polyol; or a salt and a carbohydrate and a polyol.

According to the invention the density of the metabolite and the cells are determined where after an adequate density for the aqueous liquid is found.

The density of the cells or cell derbies and the metabolite may be determined using a density gradient and separating these particles by gravimetric force.

The density gradient can be prepared as described in numerous literature references such as Brock, R. M. and Ling, N.-S., Anal. Chem. Vol. 26, page 1543, 1954 and further reviewed by Morris, C. J. O. R, and Morris, P., Separation Methods in Biochemistry, Pitman Publishing $2^{nd}$ edition 1976.

Heavy phase density may be prepared by carbohydrate solutions, e.g., sucrose, or salt solutions such as $CaCl_2$ solutions. When applying a sugar solution one should take into account that precipitated metabolites may be re-dissolved in such solutions. When applying a salt solution one should take into account that the salt may cause coagulation of the cells and cell debries affecting both density and particle size.

According to the invention a combination solution is preferred of primarily carbohydrate(s) to enhance density, and Sodium or Potassium salts with a low ion strength are added to prevent solubilization of the precipitated metabolites.

In order to test if the heavy phase density liquid has a solubilizing effect on the precipitated metabolite (e.g. protein) at the pH and temperature used during the separation, simple solubility tests can be carried out by adding a sample of the precipitated metabolite (e.g. protein) of interest to solutions of different carbohydrates and/or polyols and/or salts having the desired density and then test if the metabolite (e.g. protein) dissolves after 30 minutes of incubation. The solubility can be followed by, e.g., visual inspection or by measuring the increase of, e.g., the enzyme activity in the soluble phase.

According to the invention the aqueous liquid comprising the salt and/or the carbohydrate has a density of from 1050 kg/m3 to 1300 kg/m3; preferably the aqueous liquid comprising the salt and/or the carbohydrate has a density of from 1055 kg/m3 to 1275 kg/m3; preferably the aqueous liquid comprising the salt and/or the carbohydrate has a density of from 1060 kg/m3 to 1250 kg/m3; preferably the aqueous liquid comprising the salt and/or the carbohydrate has a density of from 1065 kg/m3 to 1225 kg/m3; preferably the aqueous liquid comprising the salt and/or the carbohydrate has a density of from 1070 kg/m3 to 1200 kg/m3; in particular the aqueous liquid comprising the salt and/or the carbohydrate has a density of from 1075 kg/m3 to 1150 kg/m3.

The aqueous liquid should preferably have a density 5-250 g/L higher than that of the particulate material not wanted in the product output, and 20-200 g/L lower than that of the precipitated metabolite desired to be recovered by the separation of the invention.

Crystalline and/or amorphous suspension

The suspension achieved according to the invention may be the final product, or the suspension may be concentrated and/or purified as known in the art, e.g., by using grinding, sieving, drying, filtration, centrifugation, re-crystallisation, chromatographic methods, adsorption processes, two-phase extraction, ultra-filtration, micro-filtration and/or evaporation.

The invention is further illustrated in the following examples which are not intended to be in any way limiting to the scope of the invention as claimed.

EXAMPLE 1

Harvest of protease crystals from fermentation broth

A fermentation broth containing a protease variant was produced in a *Bacillus licheniformis* host cell. The protease variant (Y167A+R170S+A194P) may be produced as disclosed in EP 0 583 339.

Principle:

As a model for a continuous centrifuge separation step, a traditional laboratory centrifuge was used in a batch mode wherein an aliquot of a salt and/or carbohydrate solution with the desired solution was transferred to centrifuge tubes and on top of this solution an aliquot of the fermentation broth containing both microbial cells and the metabolite in a partly precipitated form was carefully placed ensuring that the two liquids were not mixed. The tubes were then placed in the centrifuge and centrifuged at a selected set of conditions. After centrifugation the resulting phases were separated and the concentration of the metabolite in each phase was determined.

Experiment A: Separation of a protease variant from a fermentation broth

Lab. scale separation using 50 mL centrifuge tubes was used illustrating the principle of the invention.

The fermentation broth was characterized as having a liquid density of 1074 g/L at ambient room temperature of 20-25° C. (The density was determined by weighing a 100 mL sample in a measuring glass).

A crude density separation using sucrose gradient with 5% w/w sodium sulphate characterized the bacterial cells as having a density ranging from that of the liquid to 1100 g/L and bulk precipitated protease as having density ranging from 1250 to 1300 g/L at ambient room temperature.

25 mL 5% w/w sodium sulphate and 35% w/w sucrose with a combined density of 1150 g/L (ambient room temperature of 20-25° C.) was added to the centrifuge tube (high density liquid).

On top of this liquid, 25 mL of the fermentation broth containing the protease variant of interest in a (partly) precipitated form and the Bacillus licheniformis host cells was carefully layered.

The sample was centrifuged in a Heraeus Multifuge 3SR centrifuge at 4500 RPM for 6 minutes at ambient temperatures.

This condition is equal to a production scale loading of 100 L/h per 1,000 Area equivalents in a continuous flow production centrifuge. Area equivalents were calculated based on the theory first stated by C. M. Ambler, The evaluation of centrifuge performance, Chem. Eng. Prog. Vol. 48 (3), 1952, p 150-158.

After centrifugation, the sample was split into the following 3 phases:

Upper phase containing cells (25 mL),

Middle phase containing the high density liquid (first 10 mL), and

Bottom phase containing the high density liquid with precipitated protease.

The phases were separated by pipetting them off from the top.

The volume fraction in each was determined by volumetric reading and confirmed by weighing, and the supernatant, the middle phase and the bottom phase (harvest fraction) were analyzed for protease activity.

Results:

The resulting removal of the protease from the fermentation broth was 95.2%. Only a loss of 0.8% of the protease was found in the top 10 mL of the sodium sucrose solution resulting in a minimum concentration factor of 1.58 in the bottom 15 mL.

The protease was further concentrated by a secondary centrifugation of the bottom phase (15 mL) at 4500 RPM for 10 minutes. After centrifugation two phases could be seen. The bottom phase having a volume of approximately 6 mL contained the precipitated protease in an amount corresponding to a concentration factor of 4 for this specific fermentation.

Experiment B

Separation was up-scaled to a larger laboratory centrifuge Sorval RC-3B using 1 L tubes. 300 mL of 25% w/w sodium sulphate with a density of 1233 g/L was added first and on top of this liquid 500 mL fermentation broth was carefully layered.

This tube was centrifuged at 3000 RPM for 8 minutes at ambient room temperatures of 20-25° C., equal to a production scale loading of 170 L/h per 1,000 Area equivalents in a continuous flow production centrifuge.

The removal of the protease from the fermentation broth was 94.6%. 9.4% of the total activity was found in the top 200 mL of sodium sulphate solution, and the bottom 100 mL product showed an activity concentration increase of a factor 3.2.

Experiment C

An experiment similar to experiment B was performed using 300 mL of 60% w/w glycerol with a density of 1158 g/L for harvesting showed a 91.2% removal of the protease of interest from the fermentative broth.

7.5% of the total activity was found in the top 200 mL, and a product concentration increase of 3.6 times was found in the bottom 100 mL.

EXAMPLE 2

Harvest of Protease Crystals from a Fermentation Broth in a Continuous Centrifuge Process A fermentation broth containing a protease was produced in a Bacillus licheniformis host cell. The protease (Y167A+ R170S+A194P) is disclosed in, e.g., WO 98/20115. The protease is the same as used in Example 1.

Pre-treatment of the fermentation broth

The fermentation broth comprising the Bacillus licheniformis host cells and the protease of interest was diluted 20% by weight with a 12% Sodium Chloride solution. The addition of Sodium Chloride provided a high (1.5%) content of Chloride in the broth feed that could be traced in the harvesting liquid as a liquid impurity.

Characterization of metabolite/precipitated protein

The precipitated protease protein was crystalline and had a characteristic average rectangular form of 2 by 2 by 8-15 micrometer in size. A small fraction reached sizes of 5 by 5 by 50 micrometer in size.

The particle size distribution was recorded using a FBRM Probe model D600R with IC FBRM software version 4.1969 from Mettler Toledo.

Samples of 10 mL were diluted into 200 mL using tap water. The probe was immersed in the instrument. Characteristic particle size distribution in the range from 1-1000 micrometer was recorded within 30 seconds. The particle size distribution remained constant for several minutes.

The fermentation cell, Bacillus licheniformis, had a characteristic form of 1 by 1 by 2 micrometer.

The content of viable Bacillus cells was determined using a general viable count determination method. The viable count was determined to be $22\text{-}24\times 10^9$ by repeated sampling throughout the trials.

A volumetric determination of the precipitated proteins and other larger size particles was conducted by applying 5 mL broth sample on top of a heavy phase liquid (12% Sodium Sulphate or 38% Glycerol) in a 10 mL centrifuge tube and spinning this sample for 6 minutes at 3600 RPM (in Heraeus Biofuge Primo Centrifuge).

Thereafter the top fraction (5 mL) was removed, and the harvested particles in the bottom fraction (5 mL) were compacted at 3600 RPM for 10 minutes.

The solids volume recorded was related to the initial sample volume and recorded as volume %. The volumetric content was determined to be 10-11%. Density of the partial diluted broth feed was determined as 1062 g/L, and without precipitated proteins and larger particles the liquid density was determined to be 1057-1060 g/L by inline mass-flowmeter.

The Alfa Laval Separator Centrifuge MBQX illustrated in FIG. 1 was equipped with 9 peripheral nozzles 0.8 mm in size and operated at 6600 RPM speed. At the operated speed this provided a theoretical separation area of 40,000 m$^2$.

A1: An approximately 12% Sodium Sulphate solution having a density of 1097-1099 g/L was used as the heavier aqueous liquid. The optimal flow of heavy liquid was identified testing a flow range of 85-102% of the nozzle flow (2600 L/h). The flow difference between heavy liquid and nozzle flow defines a relative volume flow of particles and liquid from broth feed to the nozzles defined as the recovering flow, and this flow can be related relatively to the actual broth feed flow. The flow ranges tested was equal recovering flow of 20 to −2% of the broth feed flow of 2000 L/h.

A recovering flow of 5% of the feed flow was then chosen for the following trials. Longer duration trials using different broth flow of 2000, 4000 and 6000 L/h demonstrated the full scale application of the continuous process on this product.

Results of the trials are listed in Table 1. Yields, protein concentration factor and reduction factor of Chloride content are related to the feed volume applied. Solids volume % and viable *Bacillus* cell counts reduction are based on absolute measurements.

A2: An approximately 38% Glycerol solution having a density of 1098-1100 g/L was used as the heavy aqueous liquid. The optimal flow of the heavy liquid was identified testing a flow range of 85-102% of the nozzle flow at a broth feed flow of 2000 L/h. Again the recovering flow of 5% of the feed flow was shown to be an optimal compromise between yield and purity.

TABLE 1

| Experiment | A1 | A1 | A1 | A1 | A2 |
|---|---|---|---|---|---|
| Feed flow L/h | 2000 | 2000 | 4000 | 6000 | 2000 |
| Heavy liquid phase | 12% Na2SO4 | 12% Na2SO4 | 12% Na2SO4 | 12% Na2SO4 | 38% Glycerol |
| Protein recovered % | 83.1 | 87.9 | 90.2 | 88.4 | 89.2 |
| Protein concentration factor | 0.62 | 0.66 | 1.45 | 2.2 | 0.67 |
| Solids volume of proteins | 9 | 9 | 14 | 20 | 6 |
| Reduction factor of viable *Bacillus* cells | 4400 | 3600 | 3000 | 2900 | n.a. |
| Reduction factor of feed Chloride content | 21 | 18.6 | 19.9 | 20.2 | 20.9 |

Comments:

Particle size measurements of the recovered precipitated protein showed no significant difference in size when compared with the size measured in the fermentation broth, using the same method.

Viable count showed a reduction of more than 2000 in the cell content (from about 22,000 millions to about 5-7 millions).

The Chloride traces showed an approximate 5% liquid impurity carry-over to the harvesting liquid.

The invention claimed is:

1. A method for producing a crystalline and/or amorphous metabolite suspension from a cell fermentation broth in a continuous centrifuge process comprising
   (a) adding at a first separate inlet to the centrifuge the fermentation broth comprising the cells and the metabolite of interest, wherein the metabolite is partly or wholly in crystalline and/or amorphous form;
   (b) adding at a second inlet to the centrifuge an aqueous liquid comprising a salt and/or a carbohydrate having a higher density than the cells and a lower density than the metabolite of interest in its precipitated form;
   (c) removing the cells at a first separate outlet to the centrifuge; and
   (d) removing the suspension comprising the crystalline and/or amorphous metabolite of interest at a second outlet to the centrifuge.

2. The method according to claim 1, wherein the metabolite is a protein.

3. The method according to claim 2, wherein the protein is an enzyme.

4. The method according to claim 3, wherein the enzyme is a protease, a lipase, a cellulase, an amylase, a mannanase or an oxidoreductase.

5. The method according to claim 1, wherein the cell is a bacterial or a fungal cell.

6. The method according to claim 5, wherein the bacterial cell is a *Bacillus* cell.

7. The method according to claim 1, wherein the salt is selected from the group consisting of sodium, potassium, calcium and magnesium salts.

8. The method according to claim 1, wherein the carbohydrate is selected from the group consisting of glucose, sucrose and maltose.

9. The method according to claim 1, wherein the carbohydrate is a polyol selected from the group consisting of glycerol, sorbitol and monopropylene glycol (MPG).

10. The method according to claim 1, wherein the liquid comprising the salt and/or the carbohydrate has a density of from 1050 kg/m3 to 1300 kg/m3.

11. The method according to claim 1, wherein the outlet from the centrifuge comprising the crystalline and/or amorphous metabolite of interest is re-circulated to the second inlet.

12. The method according to claim 1, wherein the suspension comprising the crystalline and/or amorphous metabolite of interest is concentrated a factor 1.1-20 compared to the cell fermentation broth.

* * * * *